United States Patent

Radons et al.

[11] Patent Number: 5,605,150
[45] Date of Patent: Feb. 25, 1997

[54] ELECTRICAL INTERFACE FOR A PORTABLE ELECTRONIC PHYSIOLOGICAL INSTRUMENT HAVING SEPARABLE COMPONENTS

[75] Inventors: Stephen W. Radons, Snohomish; George H. Manset, Woodinville; Steven L. King, Kirkland; Randall D. Mills, Woodinville; Curt C. Johansen, Everett; Richard C. Nova, Kirkland, all of Wash.

[73] Assignee: Physio-Control Corporation, Redmond, Wash.

[21] Appl. No.: 334,625

[22] Filed: Nov. 4, 1994

[51] Int. Cl.⁶ .............................. A61B 5/00; A61B 19/00; A61B 19/02
[52] U.S. Cl. .............................. 128/630; 607/1; 128/897; 439/247; 439/248
[58] Field of Search .................................. 128/630, 897; 607/4, 5, 1; 439/247, 248, 378

[56] References Cited

U.S. PATENT DOCUMENTS

| 4,096,856 | 6/1978 | Smith et al. | 607/5 |
| 4,097,113 | 6/1978 | McKelvy | 339/256 R |
| 4,590,943 | 5/1986 | Paull et al. | 607/5 |
| 4,980,800 | 12/1990 | Furuta | 439/378 |
| 5,078,615 | 1/1992 | Benson et al. | 607/5 |
| 5,184,964 | 2/1993 | Douty et al. | 439/247 |
| 5,385,481 | 1/1995 | Kotyuk | 439/248 |
| 5,391,091 | 2/1995 | Nations | 439/378 |
| 5,487,751 | 1/1996 | Radons et al. | 607/1 |
| 5,514,000 | 5/1996 | Krause et al. | 439/248 |
| 5,529,063 | 6/1996 | Hill | 128/630 |

Primary Examiner—William E. Kamm
Assistant Examiner—Carl H. Layno
Attorney, Agent, or Firm—Christensen O'Connor Johnson & Kindness PLLC

[57] ABSTRACT

A first electrical connector of an interface is provided on a floating plug assembly mounted on one component of a physiological instrument. A second electrical connector of the interface is mounted in a socket assembly constructed in another component that can be coupled to the first component by relative linear translation. Guides located in the socket assembly capture fingers on the plug assembly as the plug assembly is inserted in the socket assembly. The guides orient the plug assembly so that the first connector is correctly aligned with the second connector. The connectors are automatically joined as the first component is coupled to the second component.

14 Claims, 5 Drawing Sheets

ELECTRICAL INTERFACE FOR A PORTABLE ELECTRONIC PHYSIOLOGICAL INSTRUMENT HAVING SEPARABLE COMPONENTS

FIELD OF THE INVENTION

This invention generally relates to portable electronic physiological instruments, and more particularly to an improved electrical interface for linking portable physiological instruments having separable first and second components.

BACKGROUND OF THE INVENTION

A well equipped emergency medical technician (EMT) typically carries a portable defibrillator/monitor which allows the EMT to monitor or defibrillate a patient's heart. Several alternative constructions have been adopted by manufacturers of portable physiological units. The assignee of the current invention, Physio-Control Corporation of Redmond, Wash., has adopted a portable construction wherein the physiological unit has two components, an ECG monitor and a defibrillator. Such a construction is described in U.S. Pat. No. 4,096,856 titled "Portable Electronic Physiological Instrument Having Separable First and Second Components, and Improved Mechanical Connector Therefor" (herein incorporated by reference). In U.S. Pat. No. 4,096,856, a physiological instrument was disclosed that had first and second components that could be coupled together by sliding a grooved member located on one of the components onto a tongue member located on the other component. The tongue-and-groove construction allowed the two components to be mechanically attached together. When defibrillation and monitoring was required, both components could therefore be carded to the scene of an accident. When only monitoring was to be performed, however, the units could be separated, and only the monitor used. This construction has proved to be reliable and intuitive to use, and has gained wide-spread acceptance among emergency medical technicians.

While the tongue-and-groove mechanical connection of a defibrillator and monitor has proven to be a very flexible and successful design, there are still some disadvantages to connecting portable physiological devices in this manner. One of the problems presented by connecting two components with a sliding connector was designing an electrical connection that would allow the units to function cooperatively, such as by exchange of data or timing and control signals.

U.S. Pat. No. 4,097,113 to McKelvy titled "Electrical Connectors for Portable Electronic Physiological Instruments Having Separable First and Second Components" disclosed an electrical connector that was developed for interfacing a first and second component that were joined by a sliding tongue-and-groove (herein incorporated by reference). The electrical connector disclosed in McKelvy is constructed with opposing sets of leaf spring contacts, each set being wrapped around a central contact support member on the respective component. When the components were slid relative to each other to make the mechanical connection, the sets of electrical contacts were brought into engagement with each other. This allowed power and other signals to be transmitted between the defibrillator and the monitor.

While the electrical interface disclosed in McKelvy was sufficient for early defibrillators and monitors, its shortcomings arose as monitors and defibrillators became more complex. Most problematic was that the McKelvy connector was only able to provide limited communication capacity between the monitor and the defibrillator. As :monitors and defibrillators offering more complex functions were considered, it became desirable to pass additional control information and signals between the two components. The McKelvy design, while reliable and sturdy, is limited with respect to the number of communication lines provided, and also is a custom connection not adapted for use with commercially available multipurpose interfaces.

SUMMARY OF THE INVENTION

The present invention provides a novel electrical interface for electrically connecting separable components of a portable physiological instrument that are joined by a tongue-and-groove mechanical interface. The electrical interface allows a standard connector on one component to be automatically aligned and connected with a matching connector on a second component as the components are slid together. The interface comprises a floating plug assembly mounted on one of the components and a corresponding socket constructed in the other component. The floating plug assembly includes two guide fingers that extend substantially parallel with the path that a connector on the plug assembly must travel in order to mate with a complementary connector located in the socket. The socket constructed in the second component has a set of guiding surfaces formed by the walls of the socket. The guiding surfaces are designed to capture the guide fingers of the plug assembly, and direct the motion of the plug assembly so that its connector automatically mates precisely with the socket connector.

Three levels of alignment are therefore provided by the electrical interface. A gross alignment is based on the mechanical interface between the first and second components. As the two components are slid together, the tongue-and-groove mechanical connection orients the connectors along substantially the same line.

An intermediate alignment is provided as the fingers of the plug assembly carrying one part of the connector are brought into contact with the guiding surfaces formed in the socket. As the first component is slid into the second component, the plug assembly is shifted into more precise alignment with the socket. The guiding surfaces form grooves that are broad at the point where the fingers first come into contact with the grooves, and taper until they are approximately the same width as the fingers. The broad width of the grooves at their start allows the fingers to be captured even if the plug assembly is slightly misaligned. As the two components are slid farther together, the plug assembly is shifted toward the socket connector by the fingers which travel down the set of grooves. When the grooves have narrowed to the size of the fingers, the plug assembly is properly oriented, and the connectors are nearly in contact.

The final precise alignment is provided by guide pegs and holes on the connectors themselves. The guide pegs and holes ensure that the contact pins in one connector accurately fit in the contact sleeves of the other connector without bending. When the two components of the portable physiological unit have been fully mated, the plug assembly connector will have been accurately guided into connection with the socket connector.

It will be appreciated that the above electrical interface offers many advantages over prior designs. Most importantly, the improved electrical interface greatly expands the communication capability between the two components, while keeping the advantages afforded by the tongue-and-groove mechanical connection in a portable physiological unit. The new connector allows multiple data or power lines to be used to couple a defibrillator to a monitor.

It is a further advantage of this interface that the use of grooves and guide fingers to accurately guide one of the connectors into the other connector ensures that the connectors will not be damaged during insertion. An unskilled user may quickly and easily slide the first component into the second component in order to make both the electrical and mechanical connections. The two connectors are brought into contact with each other automatically and with the correct orientation. This prevents damage to the connectors or their mountings.

It is also an advantage that both connectors are enclosed when the components are mated. It is therefore nearly impossible to inadvertently come in contact with them.

Finally, it will be appreciated that the above construction allows for manufacturing inaccuracies or less-than-perfect tolerances in the fit between the first component and the second component. The use of a floating plug assembly ensures that even if the components are slightly misaligned as they are being slid together, the connectors will be accurately joined as the plug assembly is guided to the proper orientation by the guides of the second component. This allows the portable physiological units to be constructed inexpensively, since close tolerances do not have to be maintained.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
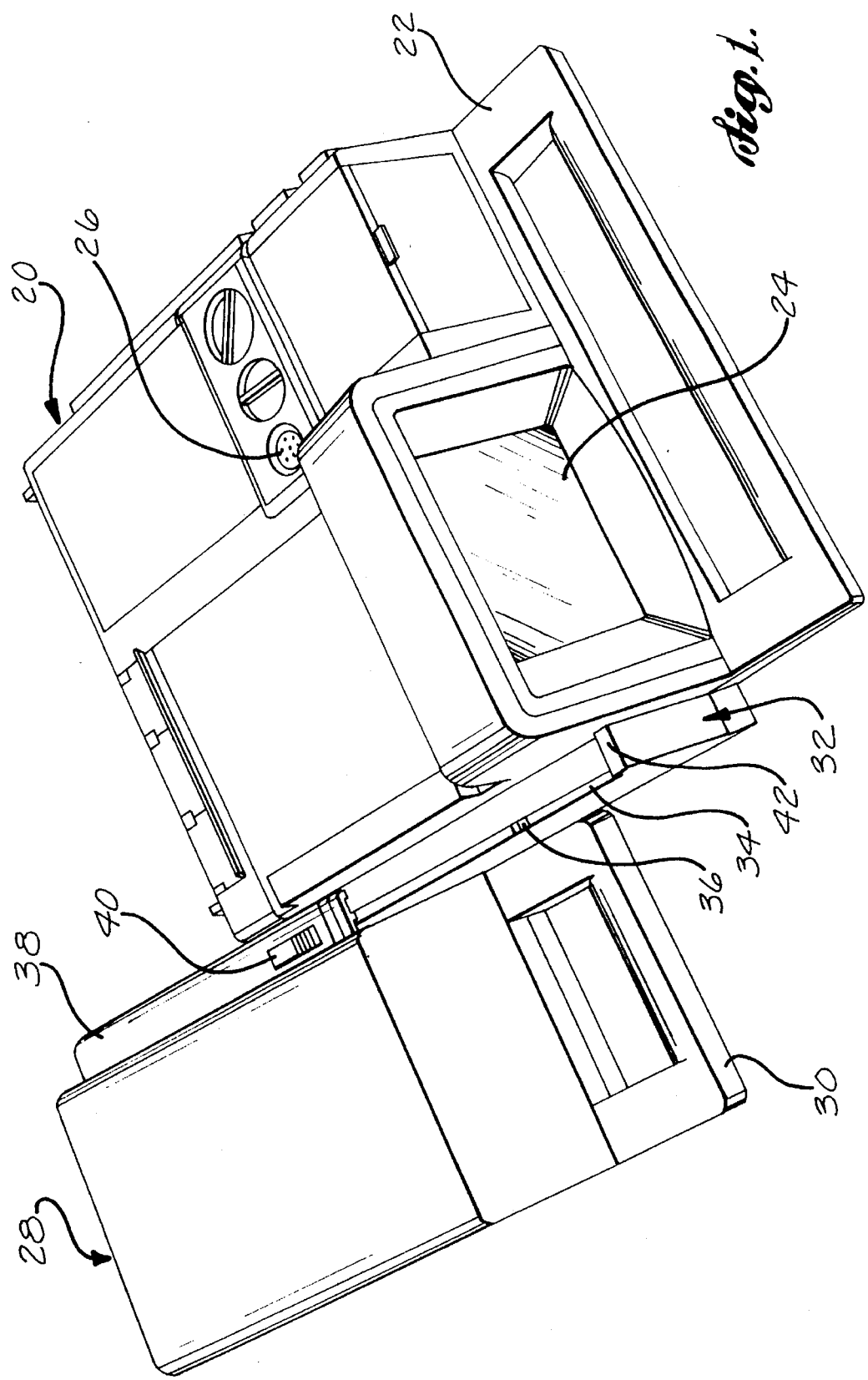
FIG. 1 is a top front perspective of a portable monitor in the process of being connected to an auxiliary component using a tongue-and-groove mechanical interface, the monitor and auxiliary component having an electrical interface in accordance with the present invention.

FIG. 1 shows a two-component portable physiological instrument having the novel electrical interface of the present invention. The first component, monitor 20, is a portable electrocardiogram (ECG) monitor/recorder which allows an EMT to record an electrocardiogram of a patient at an accident site. Monitor 20 includes a carrying handle 22 and a LCD display 24 for displaying the electrocardiogram of the patient. The electrocardiogram is taken by connecting a set of electrodes to a connector 26 located on the upper surface of monitor 20. Monitor 20 is an entirely self-contained unit, having a central processing unit, memory, and associated battery packs to operate the device. Portable ECG monitors/recorders are well known in the art, having been in existence since the late 1960s.

An auxiliary component 28 can be connected to monitor 20. The auxiliary component may perform a number of different functions which complement the operation of monitor 20. For example, the auxiliary component 28 can act as a data storage device to record electrocardiograms that have been taken from patients at accident sites. Alternatively, the auxiliary component 28 could be used to provide a communication link from the monitor 20 to other devices. The communication link may involve the transmission of an ECG over a land line connection, or via a cellular network using a cellular modem. Yet another function auxiliary component 28 could perform is as a unit for monitoring vital signs other than the patient's electrocardiogram. For example, the unit could be used to monitor a patient's $SAO_2$, End Tidal $CO_2$, or NIBP. Those skilled in the art will recognize that there are a variety of other uses for an auxiliary component that is attached to a portable monitor.

In order to function as a whole, however, auxiliary component 28 must be electrically mated with monitor 20. For convenience, the two components should also be mechanically mated. The mechanical interface ensures that the monitor and the auxiliary component may be transported as a single unit. The mechanical interface must therefore be strong, reliable, and easy to use. The electrical interface allows the two units to exchange data, and to provide other necessary signals such as power or control information. The electrical interface must also be strong, reliable, and easy to use. Unless the mechanical and electrical interfaces meet all of the above criteria, the monitor/auxiliary component instrument will not be truly portable.

As shown in FIG. 1, the mechanical interface between auxiliary component 28 and monitor 20 is a tongue-and-groove system. Those skilled in the art will recognize that the tongue-and-groove system used to connect the monitor with the auxiliary component is essentially that disclosed in U.S. Pat. No. 4,096,856 entitled "Portable Electronic Physiological Instrument Having Separable First and Second Components, an Improved Mechanical Connection Therefor" which is expressly incorporated by reference herein. While the tongue-and-groove system disclosed in that patent has been slightly modified to provide for a slightly broader tongue member, the construction is generally the same. Consequently, the patent should be consulted if more detail is desired than that provided herein.

A tongue member 32 is formed on the left side of the housing of monitor 20. The tongue member 32 has an upper tongue 34 projecting toward the upper surface of the monitor and spaced outward from the adjacent sidewall of the monitor housing. Similarly, tongue member 32 has on its lower extremity a bottom tongue (not shown) projecting toward the bottom surface of the monitor, in vertical alignment with upper tongue 34. Each tongue extends substantially the entire length of monitor 20, and is generally parallel with the adjacent wall of the monitor housing. A notch 36 is provided in upper tongue 34 near the front of the monitor for receiving a nose portion of a swinging latch 40. The top edge of upper tongue 34 terminates in a downwardly sloping surface located adjacent to the rear of monitor 20. Likewise, the bottom edge of the bottom tongue terminates in an upwardly sloping surface located adjacent to the rear of the monitor.

Formed in the fight side of the housing of auxiliary component 28 is an upper angle flange 38, toward the top of the auxiliary component, and a lower angle flange (not shown), toward the bottom surface of the auxiliary component. The angle flanges define grooves opening toward each other for receiving the corresponding tongues of monitor 20. That is, the upper angle flange 38 hooks over the top of upper tongue 34 on monitor 20, and the lower angle flange fits around the bottom margin of the lower tongue. The flanges and the tongues are complementary in configuration and lie in close proximity to each other when the tongues are inserted into the corresponding grooves.

Auxiliary component 28 is brought into mechanical connection with monitor 20 by translating the auxiliary component from the back to the front of the monitor. The angle flanges slide along the tongues as the parts are connected. The motion required to attach the auxiliary component to the monitor must be substantially linear and parallel to the left side of the monitor. For the purposes of this description, the linear path that the auxiliary component must be moved in order to engage the auxiliary component with the monitor will be referred to as the "engagement path." FIG. 1 shows the components in the process of being connected.

When the front edge of the upper flange 38 on auxiliary component 28 has slid almost the entire length of the monitor, it comes into contact with a substantially vertically extending stop member 42. The stop member ensures that auxiliary component 28 will not slide beyond the forward-most position it is to reach in relationship with monitor 20. When auxiliary component 28 has reached the front of the unit, latch 40 automatically swings in a direction to latch the two units together. Latch 40 is biased by a torsion spring, not shown, which rotates the latch into a position where a nose portion of the latch is inserted into notch 36. This prevents auxiliary component 28 from sliding further to the front of the monitor and also prevents the auxiliary component from inadvertently sliding off the rear of the monitor.

Those skilled in the art will recognize that the mechanism for connecting auxiliary component 28 with monitor 20 is that disclosed in U.S. Pat. No. 4,096,856. The tongue-and-groove connection used to connect auxiliary component 28 is, however, slightly wider to accommodate the electrical interface in accordance with the present invention which is located at the rear of the unit.

Figure 2:
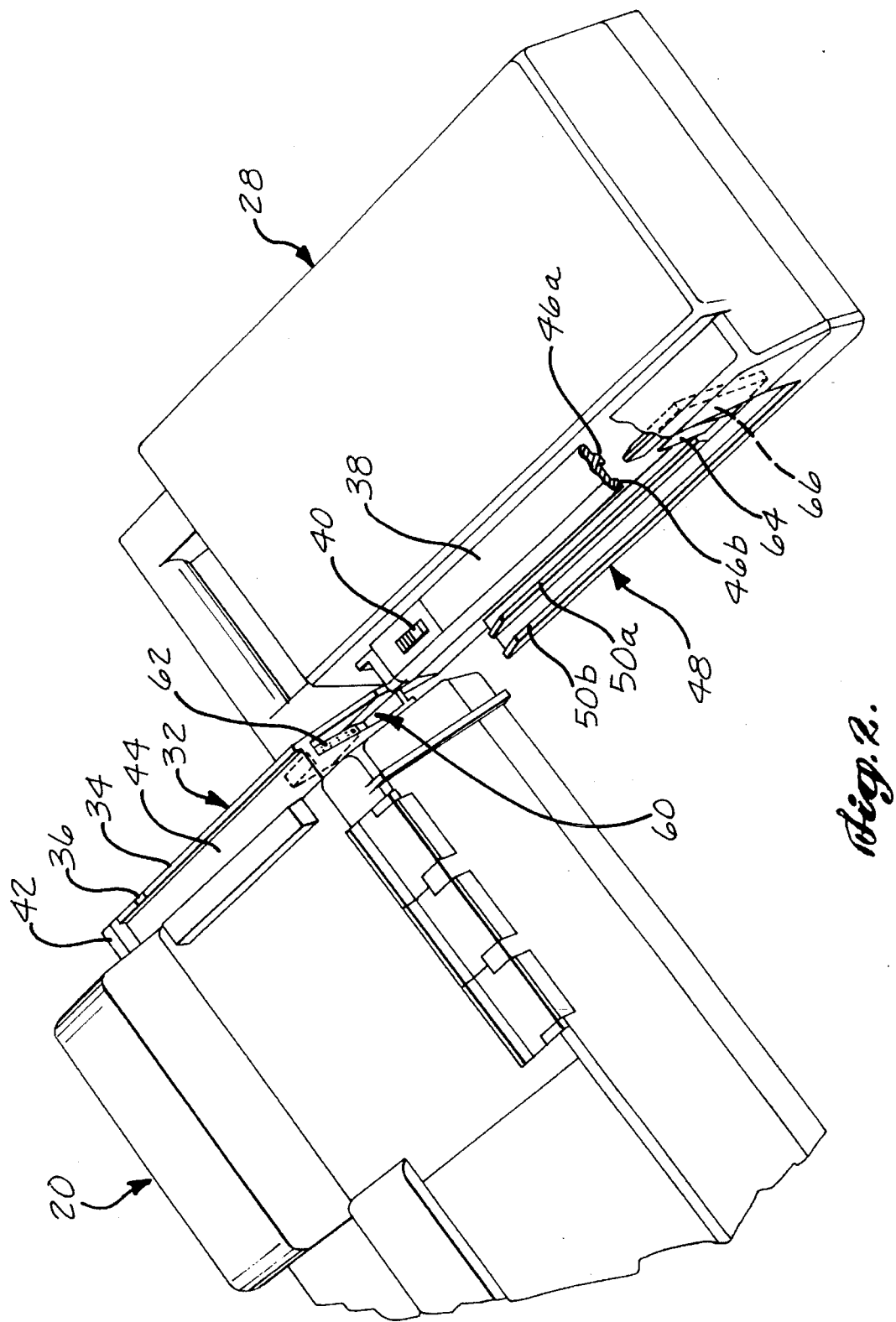
FIG. 2 is a top rear perspective of the monitor and the auxiliary component of FIG. 1.

FIG. 2 shows the rear of monitor 20 and the rear of auxiliary component 28, so that the mechanical linkage between the monitor and the auxiliary component can be seen with additional detail. For example, upper angle flange 38 is shown partially cut away so that the internal structure of the member can be seen. The upper flange has two short arms which protrude downward from the horizontal upper portion of the flange. A first arm 46a is positioned so that the groove formed between first arm 46a and the exterior right side of the housing of auxiliary component 28 is sized to receive the upper tongue 34 of monitor 20. A second arm 46b protrudes downward from the outer edge of the horizontal upper portion of the flange. Second arm 46b is positioned so that the distance between the outer upright face of second arm 46b and the inner upright face of first arm 46a is slightly less than the transverse width of a trough 44 formed by the space between upper tongue 34 and the adjacent wall of the monitor housing. The first and second arms extend the length of the upper angle flange 38, and guide the auxiliary component as it is mated with the monitor.

A similar connection is made between the auxiliary component and the monitor by a lower angle flange 48. The lower flange has a first arm 50a and a second arm 50b which protrude upward in alignment with arms 46a and 46b, respectively. The first and second arms ride in a lower trough formed in tongue member 32. Auxiliary component 28 is attached to monitor 20 by positioning the auxiliary component as shown in FIG. 2 and pulling on the auxiliary component handle toward the front of monitor 20.

As the monitor and the auxiliary component are mechanically mated, an electrical connection between the components must be made in order for the auxiliary component to interact with the monitor. FIG. 2 provides a perspective view of the electrical interface. Tongue member 32 on monitor 20 is formed with a socket 60 opening toward the rear of the monitor. Socket 60 is integrally formed with the housing of monitor 20 and has a floor, ceiling, and left, right, and rear walls. Located within socket 60 is a first connector 62. Such first electrical connector is fixedly mounted to the rear wall of socket 60 and oriented so that the connection face of the connector is generally oriented toward the rear of the monitor.

On the auxiliary component, a plug assembly 64 is located between upper flange 38 and lower flange 48. As will be described in further detail below, plug assembly 64 is loosely mounted to the housing of the auxiliary component. A second connector 66 is fixedly attached to plug assembly 64. The second connector is oriented so that its connection face is generally pointing toward the front of auxiliary component 28. As the auxiliary component is mechanically mated with monitor 20, the plug assembly is inserted into socket 60. This causes first connector 62 to mate with second connector 66, linking the auxiliary component with the monitor electrically as well as mechanically.

Figure 3:
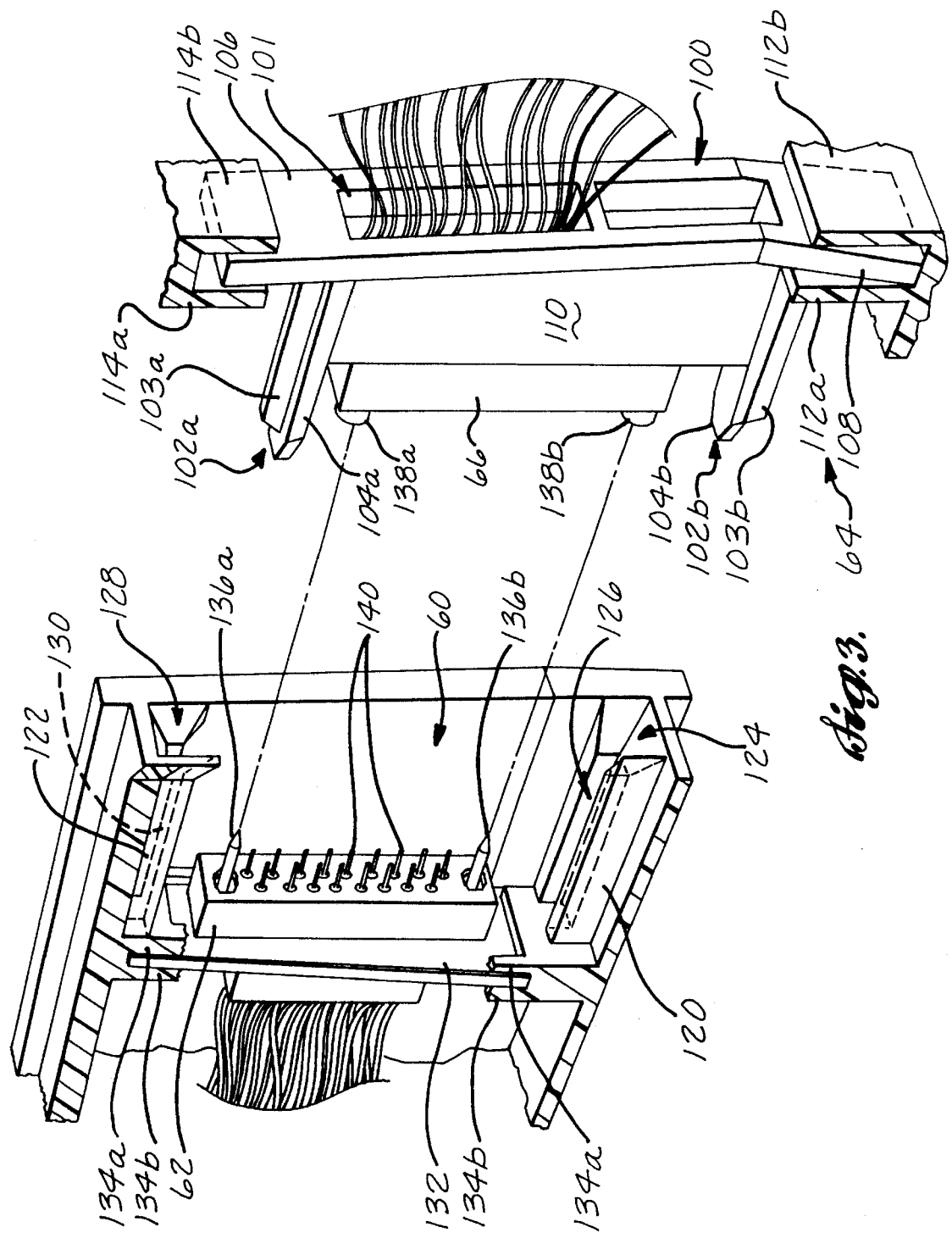
FIG. 3 is an enlarged, fragmentary, rear perspective of a plug assembly and a socket forming the preferred electrical interface between the monitor and the auxiliary component.

FIG. 3 is a detailed view of the electrical interface between the monitor and the auxiliary component, including plug assembly 64 and socket 60. Plug assembly 64 includes a back plate 100, two guide fingers 102a and 102b projecting forward from the back plate, and a body 110 joining the rear end portions of the fingers and mounting the second connector 66. The back plate is transversely oriented with respect to the engagement path and consists of a thin sheet of nonconducting material having an upper tab 106 and a lower tab 108. The black plate is also formed with a hole 101, which allows access to the rear of second connector 66. Nonconducting body 110 is integral with guide fingers 102a and 102b and back plate 100.

Each guide finger is aligned substantially parallel with the engagement path. The guide fingers are formed with vertical tongue portions 103a and 103b, and horizontal stiffening portions 104a and 104b. Tongue portions 103a and 103b are sized to fit within complementary channels formed in socket 60. The leading edge of each tongue portion is slanted generally toward the center of the plug assembly to where the tongue portions meet the stiffening portions. Tapering the forward tips of the tongue portions ensures that the portions will be reliably and smoothly guided into the complementary socket channels. Stiffening portions 104a and 104b are provided to lend strength and rigidity to the corresponding tongue portions, and also to guide the plug assembly laterally. The forward edges of the stiffening portions are beveled inward to aid the insertion into the socket.

Second connector 66 is positioned between guide fingers 102a and 102b. The second connector is fixedly mounted to the body of plug assembly 64, and is oriented so that it faces the front of the auxiliary component.

Plug assembly 64 is held in auxiliary component 28 by a series of upper and lower braces that are constructed in the auxiliary component housing. As shown in FIG. 3, the lower tab 108 is sandwiched between a lower front brace 112a and a lower rear brace 112b. The fit is snug but not tight. This allows back plate 100 to move within the limited range between the lower front and rear braces. Similarly, an upper front brace 114a and an upper rear brace 114b are positioned, respectively, in front of and behind upper tab 106. The upper front and rear braces are spaced apart a distance that is slightly greater than the thickness of the upper tab. This allows upper tab 106 to move between the upper front and rear braces. Similarly, the back plate is sized to move vertically and laterally. By loosely mounting back plate 100 between the upper and lower braces, plug assembly 64 has a limited degree of freedom to move a small amount up or down, front or back, from side to side, or to pivot slightly around a vertical axis extending between the upper and lower braces. Nevertheless, plug assembly 64 cannot be removed from the auxiliary component without physically opening the auxiliary component housing, because the housing of auxiliary component 28 extends on both sides of the upper and lower braces.

FIG. 3 also shows socket 60, which contains first connector 62 and is designed to receive plug assembly 64. The opening of socket 60 is large enough to allow the majority of the body and guide fingers of plug assembly 64 to be brought within socket 60 as auxiliary component 28 is mated with monitor 20. Back plate 100 of the plug assembly, however, remains on the outside of the socket when the two connectors are mated together.

Socket 60 is formed with two guides. A first guide 120 is formed on the floor of the socket, and a second guide 122 is formed on the ceiling of the socket. The first guide 120 has a broad sloping entrance 124 which narrows into a channel 126. Similarly, the second guide 122 has a broad entrance 128 that narrows into a channel 130. Channels 126 and 130 are sized to correspond to the width of guide fingers 102a and 102b. That is, channels 126 and 130 are sized to receive the tongue portions of the guide fingers 102a and 102b as the plug assembly is inserted into the socket. Each entrance is triangular shaped, broader near the rear opening of the socket, then tapering forward and inward until the entrance joins its channel 126 or 130. The entrances are sized to allow for some misalignment of plug assembly 64 as it is inserted into socket 60. The broader entrances capture the guide fingers regardless of misalignment due to tolerance errors in the components.

As shown in FIG. 3, entrance 124 is also slightly larger than entrance 128. The lower entrance is sized in this manner to ensure that the plug assembly will be captured within the socket when the monitor and the auxiliary component are mated in a horizontal position. As shown in FIG. 1, monitor 20 and auxiliary component 38 are typically kept horizontal as the auxiliary component is slid into connection with the monitor. When the monitor and the auxiliary component are oriented in this manner, plug assembly 64 will typically float so that upper and lower guide fingers 102a and 102b are pointed downward. As the plug assembly is brought into contact with the socket, it is therefore important to capture the lower floating guide finger in order to return the plug assembly to a position where it is generally horizontal and parallel with the engagement path. Entrance 124 is therefore sized with a slightly larger and deeper opening to ensure that guide finger 102a is captured if it is biased downward.

Returning to FIG. 3, first connector 62 is mounted to the rear wall of socket 60. The rear wall 132 of socket 60 is made of a molded flexible material such as silicone rubber around a solid plate core, which serves two purposes. First, the use of rubber provides a splash proof seal between the connector and the monitor housing. Second, the rubber with solid plate core will have a tendency to bend slightly when a force is exerted against first connector 62, allowing for some misalignment tolerance. Rear wall 132 is held in place in the monitor housing by front supports 134a and rear supports 134b that protrude from the monitor housing and tightly engage opposite sides of the wall.

As was discussed above, the gross alignment of the first connector with the second connector is performed when the angle flanges of the auxiliary component are initially slid over the tongue member on the monitor. The intermediate alignment of the first connector with the second connector occurs as the plug assembly 64 is brought into contact with socket 60. As the plug assembly is inserted into the socket, guide fingers contact entrance 124 and entrance 128. Further insertion of the plug assembly causes the tips of the guide fingers to move along the entrances toward channels 126 and 130. Eventually, the guide fingers enter channels 126 and 130, or, more specifically, the tongue portions 103a and 103b become confined within the channels. The stiffening portions 104a and 104b rest on the upper surface of the guide walls which form channels 126 and 130. At this point, the orientation of plug assembly 64 is fixed with respect to the socket, causing second connector 66 to be brought into alignment with first connector 62.

The final precise alignment of the first connector with the second connector is performed by guide pegs 136a and 136b projecting from connector 62, and by guide receptacles or holes 138a and 138b in connector 66. As the connectors are brought together, the tapered ends of the pegs are inserted into the holes. This final alignment assures that contact pins 140 on first connector 62 accurately are guided into complementary contact sleeves contained in second connector 66. As the plug assembly is fully inserted into socket 60, the second connector is thus mated with the first connector. Those skilled in the art will recognize that the mating of the two connectors completes an electrical connection between the monitor and the auxiliary component.

Figure 4:
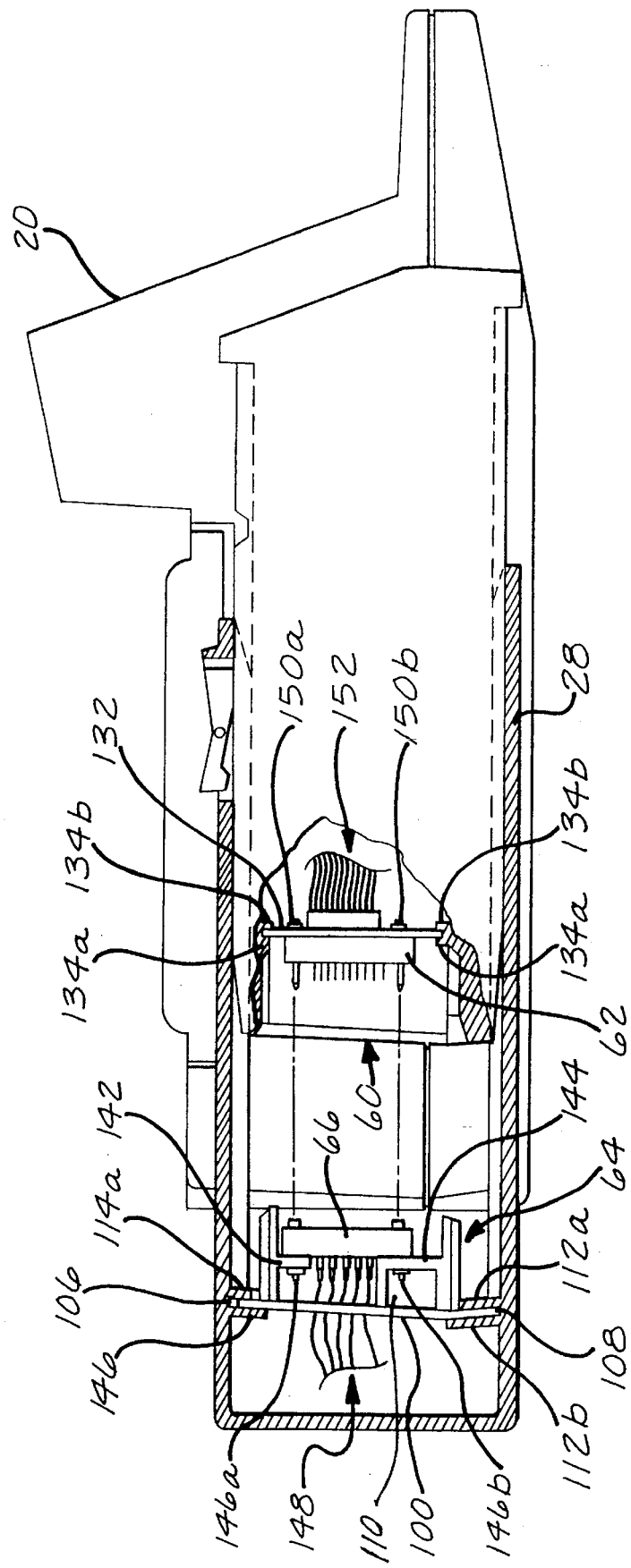
FIG. 4 is a side elevation of the monitor and the auxiliary component, with the parts broken away to reveal the plug assembly and socket as they are brought together.

The operation of the electrical interface between plug assembly 64 and socket 60 will be further appreciated with reference to FIG. 4. Lower front and rear braces 112a and 112b directly protrude from the housing of the auxiliary component to surround lower tab 108. Similarly, upper front and rear braces 114a and 114b protrude from the housing to surround upper tab 106. The braces jointly hold the back plate of plug assembly 64 oriented toward the front of the auxiliary component, yet allow plug assembly 64 a limited degree of freedom to move relative to the housing.

FIG. 4 also shows the mounting of second connector 66 to plug assembly body 110. The side of body 110 seen in FIG. 4 is hollowed to provide mounting flanges 142 and 144 to which connector 66 can be secured by bolts 146a and 146b or by screws. A set of auxiliary wires 148 are connected to second connector 66, completing an electrical linkage between auxiliary component circuitry and the connector on the plug assembly. On the other component, first connector 62 is mounted to the back wall 132 by bolts 150a and 150b. A set of monitor wires 152 are connected to first connector 62, completing an electrical linkage between the monitor circuitry and the connector in the socket.

Figure 5:
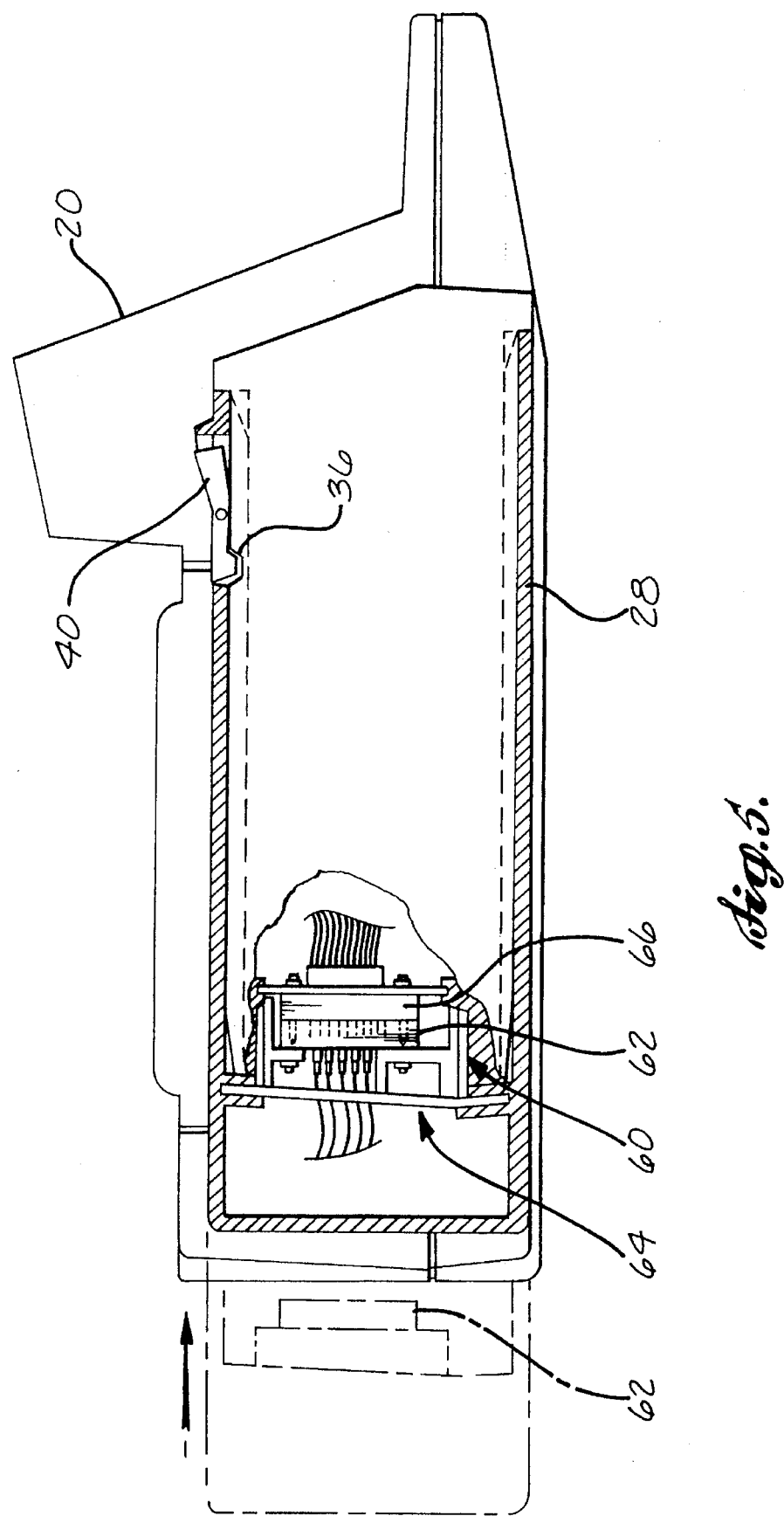
FIG. 5 is a side elevation corresponding to FIG. 4, but with the monitor and auxiliary component in different positions.

The auxiliary component 28 in FIG. 4 has only been partially slid onto the tongue member of monitor 20. The relative positions of the parts when the components are fully connected together is shown in FIG. 5.

In a preferred embodiment of the invention, first connector 62 and second connector 66 are 17 pin Hypertronics connectors, manufactured by Hypertronics Corp. as a part number FSCM 50541. The electrical connection made between the auxiliary component and monitor with the connectors includes a bidirectional serial data channel that conforms to the EIA 232 communications standard. The bidirectional serial data channel can be used to transfer patient data files including recorded ECG information, defibrillation reports, and pacing reports.

It will be appreciated that the disclosed interface provides several advantages over an exposed RS-232 port. Most importantly, the alignment between the connectors is done automatically and without user intervention, allowing the monitor and auxiliary component to be quickly connected or disconnected with ease. The automatic connection ensures good contact between the two connectors, and prevents wear and tear on either of the connectors.

It will further be appreciated that a user does not have to align first connector 62 with second connector 66 when mating auxiliary component 28 and monitor 20. The alignment is performed automatically as plug assembly 64 is guided into connection with socket 60. Further, because plug assembly 64 is mounted with limited freedom in auxiliary component 28, the alignment between the auxiliary component and the monitor can be less than exact. A slight misalignment of the two components of the portable physiological device will not affect the ability of the first connector to mate with the second connector. Additionally, when the two connectors are mated, any force placed on the two units when they are bumped or pulled apart from the sides will not affect the connection made between the first and the second connectors. Instead, plug assembly 64 will slightly rotate to ensure that the connections are not broken.

It will also be appreciated that because first connector 62 and second connector 66 are fully surrounded by socket 60, the electrical connection is protected from external contamination. The two connectors are effectively shielded by the housings of the two components to ensure that they cannot be inadvertently damaged.

While the preferred embodiment of the invention has been illustrated and described, it will be appreciated that various changes can be made therein without departing from the spirit and scope of the invention. For example, the positioning of male and female connectors is entirely arbitrary and the position of the connectors could be swapped. Further, connectors other than Hypertronics connectors could be used to electrically mate the two components. Hypertronics connectors were selected in the preferred embodiment of the invention because they are a standard part that is readily available. However, connectors having a greater or lesser number of pins could be used depending upon the function and the communication link necessary between the two components.

It will also be appreciated that sealing gaskets could be applied to the external mating surfaces of the plug assembly and the socket. This would provide additional waterproof protection of the connectors contained therein. It is an object of the appended claims to cover all modifications and variations that come within the spirit and scope of the invention.

The embodiments of the invention in which an exclusive property or privilege is claimed are defined as follows:

1. A portable electronic physiological instrument having first and second separable components and an electrical interface therebetween to allow electrical connection between the first and second components, the instrument comprising:

(a) a first component having a housing, said first component including groove member means coupled to the housing of the first component for mating the first component to a second component, said first component also including support means coupled to the housing for mounting a plug assembly to the housing so that the plug assembly has a limited freedom to move, wherein the plug assembly comprises:
  (i) a body;
  (ii) a first connector fixedly mounted to the body; and
  (iii) a pair of guide fingers extending from the body, one of the pair of guide fingers located on one side of the first connector and the other of the pair of guide fingers located on the other side of the first connector, wherein the guide fingers extend from the body in a direction that is substantially parallel with a path that the first connector must travel in order to mate with a complementary connector; and (b) a second component having a housing, said second component including tongue member means coupled to the housing of the second component, the tongue member means receiving the groove member means of the first component with a translative, sliding fit to provide mechanical interconnection between the first and second components, said second component also including a socket assembly formed in the housing of the second component, said socket assembly comprising:
  (i) a socket having a floor, a ceiling, a left wall, a right wall, and a rear wall, the walls of the socket forming an opening opposite the rear wall of the socket that is sized to receive the plug assembly;
  (ii) a second connector fixedly mounted on the rear wall of the socket and oriented to face the opening of the socket, the second connector complementary formed to mate with the first connector; and
  (iii) a pair of guides, one of the pair of guides formed in the floor of the socket and the other of the pair of guides formed in the ceiling of the socket, the set of guides substantially aligned along a path that a corresponding connector must travel to mate with the second connector, so that as the first component is slidably connected with the second component, the guides channel the guide fingers of the plug assembly and bring the first connector into alignment and eventual connection with the second connector.

2. The physiological instrument of claim 1, wherein each of the pair of guides defines a groove that extends substantially from the opening of the socket to the rear wall of the socket.

3. The physiological instrument of claim 2, wherein each groove has an entrance portion and a channel portion, the channel portion extending from the rear wall of the socket to the entrance portion and being sized to receive a corresponding guide finger of the plug assembly, the entrance portion extending from the channel portion to the opening of the socket and having a generally triangular shape that broadens from the size of the channel portion where the entrance portion meets the channel portion, to where the entrance portion meets the opening of the socket.

4. The physiological of claim 3, wherein a floor of the entrance portion of each of the pair of grooves is further sloped from the expanded opening where the entrance portion meets the opening of the socket assembly to the point where the entrance portion meets the channel portion.

5. The physiological instrument of claim 1, wherein the plug assembly further comprises a pair of guide pegs extending from the first connector, one of the pair of guide pegs located on one side of the first connector and the other of the pair of guide pegs located on the other side of the first connector, wherein the guide pegs extend from the first connector in a direction that is substantially parallel with a path that the first connector must travel in order to mate with a complementary connector.

6. The physiological instrument of claim 5, wherein the second connector a pair of holes spaced apart and sized to receive the pair of guide pegs extending from the first connector.

7. A mechanical interface for securing a monitor to an auxiliary component, where the monitor and auxiliary component include an electrical interface through which data or power can be conveyed between the monitor and the auxiliary component, the mechanical interface comprising:

(a) a groove portion disposed on a side wall of the auxiliary component, the groove portion including an upper angle flange and a lower angle flange spaced away from and parallel with the side wall of the auxiliary component;

(b) a plug assembly mounted to the auxiliary component so that the plug assembly is generally oriented parallel with the side wall of the auxiliary component and between the upper and lower angle flanges, the plug assembly mounted to the auxiliary component by support means that provide the plug assembly a limited freedom to move, said plug assembly comprising:
(i) a body;
(ii) a first connector fixedly mounted to the body; and
(iii) a pair of guide fingers extending form the body, one of the pair of guide fingers located on one side of the first connector and the other of the pair of guide fingers located on the other side of the first connector, wherein the guide fingers extend from the body in a direction that is substantially parallel with a path that the first connector must travel in order to mate with a complementary connector;

(c) a tongue member disposed on a side wall of the monitor, the tongue member having an upper tongue extending parallel with the side wall and forming a top channel between the upper tongue and the side wall of the monitor, and a lower tongue extending parallel with the side wall and forming a lower channel between the lower tongue and the side wall of the monitor, the upper and lower channels sized to receive the respective upper and lower angle flanges of the auxiliary component to engage the monitor and the auxiliary component; and (d) a socket assembly constructed in the monitor, the socket assembly having a floor, a ceiling, a left wall, a right wall, and a back wall, the walls of the socket assembly forming an opening in the socket assembly that is opposed to the back wall and is sized to receive the plug assembly, said socket assembly comprising:
(i) a second connector fixedly mounted to the back wall of the socket assembly and oriented toward the opening of the socket assembly; and
(ii) a pair of guides, one of the pair of guides formed in the floor of the socket assembly and the other of the pair of guides formed in the ceiling of the socket assembly, the set of guides substantially aligned along a path that a corresponding connector must travel to mate with the second connector, so that as the plug assembly is inserted into the socket assembly, the guides channel the guide fingers of the plug assembly and bring the first connector into alignment and eventual connection with the second connector, the first connector and second connector being substantially within the socket assembly when connected.

8. The interface of claim 7, wherein each of the pair of guides defines a groove that extends substantially from the opening of the socket assembly to the rear wall of the socket assembly.

9. The interface of claim 8, wherein each groove has an entrance portion and a channel portion, the channel portion extending from the rear wall of the socket assembly to the entrance portion and being sized to receive a corresponding guide finger of the plug assembly, the entrance portion extending from the channel portion to the opening of the socket assembly and having a generally triangular shape that broadens from the size of the channel portion where the entrance portion meets the channel portion, to where the entrance portion meets the opening of the socket assembly.

10. The interface of claim 9, wherein a floor of the entrance portion of each of the pair of grooves is further sloped from the expanded opening where the entrance portion meets the opening of the socket assembly to the point where the entrance portion meets the channel portion.

11. The interface of claim 7, wherein the plug assembly further comprises a pair of guide pegs extending from the first connector, one of the pair of guide pegs located on one side of the first connector and the other of the pair of guide pegs located on the other side of the first connector, wherein the guide pegs extend from the first connector in a direction that is substantially parallel with a path that the first connector must travel in order to mate with a complementary connector.

12. The interface of claim 11, wherein the second connector is formed with a pair of holes sized to receive a pair of guide pegs extending from a complementary connector.

13. A portable electronic physiological instrument comprising a first component having a housing, a second component having a housing, the housings of the first and second components having a cooperating tongue-and-groove joint for joining the first component to the second component by relative translation along a substantially linear path, said first and second components having an electrical interface including a first connector carried by the first component and a second connector carded by the second component, said first and second connectors having cooperating pin and socket conductors interconnectable by relative translation generally parallel to the linear path, the first and second connectors being mounted, respectively, to the first and second components substantially in alignment with reference to the linear path such that the tongue-and-groove joint achieves a gross alignment of the first connector with the second connector, the first connector being stationarily mounted on the first component, and the second connector being mounted on the second component for limited movement relative thereto in a plane perpendicular to the linear path but being restricted from movement parallel to the linear path, one of the first and second connectors having two guide fingers projecting generally parallel to the linear path toward the other of the first and second connectors as the first component is joined to the second component and such other of the first and second connectors having two guide ways generally aligned with the guide fingers as the first component is joined to the second component, the guide fingers and guide ways having cooperating tapered portions constructed and arranged relatively for interengagement so as to align the first connector with the second connector more precisely as the first and second components are moved along the linear path defined by the tongue-and-groove joint, the first connector further having a pair of guide pegs extending from the first connector in a direction that is substantially parallel with the linear path.

14. The portable electronic physiological instrument of claim 13, wherein the second connector comprises a pair of holes sized to receive the pair of guide pegs extending from the first connector.

* * * * *

UNITED STATES PATENT AND TRADEMARK OFFICE
CERTIFICATE OF CORRECTION

PATENT NO. : 5,605,150
DATED : February 25, 1997
INVENTOR(S) : S.W. Radons et al.

It is certified that error appears in the above-indentified patent and that said Letters Patent is hereby corrected as shown below:

| COLUMN | LINE | |
|---|---|---|
| 10 (Claim 1, | 24 line 51) | After "second connector" insert --, the first connector and the second connector being substantially within the socket when connected-- |
| 10 (Claim 4, | 38 line 1) | After "physiological" insert --instrument-- |
| 10 (Claim 6, | 52 line 2) | After "second connector" insert --comprises-- |
| 12 (Claim 13, | 28 line 9) | "carded" should read --carried-- |

Signed and Sealed this

Twenty-sixth Day of August, 1997

Attest:

BRUCE LEHMAN

Attesting Officer

Commissioner of Patents and Trademarks